United States Patent
Irie et al.

(10) Patent No.: US 8,861,826 B2
(45) Date of Patent: Oct. 14, 2014

(54) X-RAY CT DEVICE

(75) Inventors: Toshiyuki Irie, Hitachi (JP); Hironori Ueki, Hachioji (JP); Keisuke Yamakawa, Kokubunji (JP)

(73) Assignee: Hitachi Medical Corporation, Tokyo (JP)

( * ) Notice: Subject to any disclaimer, the term of this patent is extended or adjusted under 35 U.S.C. 154(b) by 199 days.

(21) Appl. No.: 13/384,769

(22) PCT Filed: Aug. 4, 2010

(86) PCT No.: PCT/JP2010/063210
§ 371 (c)(1),
(2), (4) Date: Jan. 19, 2012

(87) PCT Pub. No.: WO2011/030637
PCT Pub. Date: Mar. 17, 2011

(65) Prior Publication Data
US 2012/0121157 A1     May 17, 2012

(30) Foreign Application Priority Data

Sep. 11, 2009    (JP) .................................. 2009-210697

(51) Int. Cl.
*G06K 9/00* (2006.01)
*A61B 6/03* (2006.01)
*A61B 6/00* (2006.01)

(52) U.S. Cl.
CPC .................. *A61B 6/032* (2013.01); *A61B 6/504* (2013.01); *A61B 6/481* (2013.01); *A61B 6/541* (2013.01); *A61B 6/503* (2013.01)
USPC ....................................................... 382/131

(58) Field of Classification Search
USPC .......................... 382/128–134; 128/920–925; 356/39–49; 600/407–414, 424–426; 345/581–618; 250/455
See application file for complete search history.

(56) References Cited

U.S. PATENT DOCUMENTS

2010/0316270 A1* 12/2010 Erhard et al. .................. 382/128
2011/0206247 A1*  8/2011 Dachille et al. ............... 382/128

FOREIGN PATENT DOCUMENTS

| JP | 4-263841 | 9/1992 |
| JP | 8-161520 | 6/1996 |
| JP | 10-75947 | 3/1998 |
| JP | 2007-29514 | 2/2007 |
| WO | WO 2008/084352 A1 | 7/2008 |

OTHER PUBLICATIONS

Justus E. Roos, et al., Thoracic Aorta: Motion Artifact Reduction with Retrospective and Prospective Electrocardiography-assisted Multi-Detector CT, Radiology, Jan. 2002, pp. 271-277, vol. 222, No. 1.
Christopher Herzog, et al., Significant Coronary Artery Stenosis: Comparison on Per-Patient and Per-Vessel or Per-Segment Basis at 64-Section CT Angiography, Radiology, Jul. 2007, pp. 112-120, vol. 244, No. 1.

* cited by examiner

*Primary Examiner* — Atiba O Fitzpatrick
(74) *Attorney, Agent, or Firm* — Antonelli, Terry, Stout & Kraus, LLP.

(57) ABSTRACT

A view image of high time resolution acquired in an imaging process of X-ray CT is displayed. In this display, by subtracting a background image obtained by forward projection calculation of a CT image from the view image, background is removed from the view image, and only a focused site is imaged. A transmission image of the focused site showing high display contrast and not easily influenced by a motion artifact can be thereby obtained. Thereby, in an X-ray CT device for diagnostic imaging, degradation of diagnostic ability due to motion artifacts can be prevented.

15 Claims, 15 Drawing Sheets

Region of Interest

Geometric shape

○ Whole region

○ Spherical shape  Center coordinates  xo [ ] mm   Diameter d [ ] mm
                                        yo [ ] mm
                                        zo [ ] mm ● Box shape  Center coordinates  xo [50] mm   Size  wx [40] mm
                                 yo [0] mm          wy [80] mm
                                 zo [150] mm        wz [120] mm Threshold extraction

○ NO

● YES  Threshold [0] ~ [1500] HU
       Expanding range d [1.5] mm

Excluding region

● NO

○ YES  Threshold [ ] ~ [ ] HU

───────────────────────────────── 500

CT-value conversion

○ Constant [ ] HU

● Interpolation

○ NO

───────────────────────────────── 501

View image addition

Number of Addition  M [ ]

Exposure time  T [3.5] ms

Weighting function  ● Rectangular  ○ Triangular

───────────────────────────────── 502

View image creation range  Angle [0] ~ [360] deg   Step [10] deg

| View number | (condition1) Used for re-construction | (condition2) Designated for creation | (condition3) Including ROI | View for creation (1)&(2)&(3) |
|---|---|---|---|---|
| 1 | | | | |
| 2 | | | ○ | |
| 3 | | ○ | ○ | |
| 4 | | ○ | ○ | |
| 5 | ○ | ○ | ○ | ○ |
| 6 | ○ | ○ | ○ | ○ |
| 7 | ○ | ○ | | |
| 8 | ○ | ○ | | |
| ⋮ | ⋮ | ⋮ | ⋮ | ⋮ |

US 8,861,826 B2

X-RAY CT DEVICE

TECHNICAL FIELD

The present invention relates to a medical X-ray CT device, especially a technique for preventing degradation of diagnostic ability resulting from motion artifacts in CT images by providing a user with information on X-ray transmission images obtained in the CT imaging process.

BACKGROUND ART

X-ray CT devices are devices for reconstructing a tomographic image (henceforth referred to as CT image) of a subject by using X-ray transmission image data of the subject obtained by imaging with revolving a pair of oppositely disposed X-ray tube and X-ray detector on both sides of the subject, and they are widely used in the field of diagnostic imaging, and so forth. Since velocity of the aforementioned revolution in such X-ray CT devices is limited, they suffer from a problem that false images called motion artifacts are generated in CT images of moving subjects such as the heart, and degrade diagnostic ability. For solving this problem, the electrocardiography-gated scan was devised, and put into practical use. The electrocardiography-gated scan is a method of performing X-ray CT imaging with monitoring electrocardiographic waveform by using an electrocardiograph attached to a subject. In this method, a short time gate width is provided around a predetermined cardiac phase of the heart repeating a periodic motion, and image reconstruction is performed by using only imaging data obtained within this time gate width. Therefore, motion artifacts can be reduced.

The electrocardiography-gated scan is classified into two types, the prospective scan and the retrospective scan, on the basis of the difference in data acquisition scheme (refer to Non-patent document 1). The prospective scan is a method in which X-ray is irradiated in accordance with a predetermined cardiac phase on the basis of an average cardiac cycle immediately before the imaging to obtain imaging data. The retrospective scan is a method in which electrocardiac waveforms are monitored during the imaging, and only imaging data corresponding to an arbitrary cardiac phase are extracted after completion of the imaging, and used for reconstruction of CT images.

For the electrocardiography-gated scan, there have been reported cases where motions of the heart within the aforementioned time gate width cannot be completely ignored, and therefore motion artifacts remain to induce misdiagnosis. For example, in Non-patent document 2, it was reported that, in the diagnosis of coronary artery stenosis using the retrospective scan, negative predictive value (NPV) exceeded 90%, whereas positive predictive value was only about 70 to 80%. That is, there frequently occurs a case where, in spite of diagnosis of stenosis, stenosis does not actually exist. Therefore, it has a problem that it may invite need for reexamination, or it may lead to an incorrect operation in the worst case.

PRIOR ART REFERENCES

Non-Patent Documents

Non-patent document 1: Radiology, Volume 222, pp. 271-277 (2002)
Non-patent document 2: Radiology, Volume 244, pp. 112-120 (2007)

SUMMARY OF THE INVENTION

Object to be Achieved by the Invention

An object of the present invention is to provide an X-ray CT device that facilitates reduction of misdiagnosis rate, in particular, an X-ray CT device that can reduce misdiagnosis rate in diagnosis of angiostenosis using the electrocardiography-gated scan in X-ray CT.

The object and details of the novel characteristics of the present invention will be explained in detail in the descriptions of this specification and the appended drawings.

Means for Achieving the Object

In order to achieve the aforementioned object, according to the present invention, an X-ray transmission image obtained at the time of imaging of a subject with an X-ray CT device (henceforth referred to as view image) is displayed as an image to provide an inspector with novel information. In general, in the X-ray CT imaging for diagnosis, about 1000 view images of a subject are acquired in the scan during one revolution. In this case, if it is taken into consideration that the revolving speed of a common X-ray CT device is about 0.35 [second/revolution], the imaging exposure time of each view image is about 0.35 [ms], and thus sufficiently high time resolution is realized for the motion of the heart. That is, motion artifacts hardly exist in such view images, and therefore whether angiostenosis is present or not can be judged by confirming the view images. However, in many cases, besides the information on the objective blood vessel, information on other organs such as the heart and bones (henceforth referred to as background information) is also imaged on the view images so as to overlap with the objective information, and therefore it is not easy for an inspector to detect an objective blood vessel or judge whether stenosis is present or not. Therefore, according to the present invention, a view image of only the background information (henceforth referred to as background view image) is created by forward projection operation of a CT image, and by obtaining difference of the view image and the background view image, a differential view image, in which the background information is eliminated, is created and displayed.

Specifically, the X-ray CT device of the present invention comprises an X-ray generating part, an X-ray detecting part oppositely disposed to the X-ray generating part, a revolving mechanism part for revolving a pair of the X-ray generating part and the X-ray detecting part, an image processing part for creating a CT image of a subject on the basis of X-ray transmission images of the subject acquired at a plurality of positions along the circumferential direction of the revolution, and a display part for displaying the CT image, wherein the image processing part comprises a region-of-interest setting part for setting a region of interest in the CT image, a data value converting means for converting a data value of the CT image in the region of interest to a predetermined constant value or another value obtained by calculation, a forward projection means for performing forward projection of the CT image in which the data value has been converted from a virtual X-ray generating part to a virtual X-ray detecting part to calculate a pseudo X-ray transmission image, and a difference calculating means for calculating difference between the X-ray transmission image and the pseudo X-ray transmission image to create a differential image. As the X-ray image and the pseudo X-ray transmission image used for creating the differential image, there are used those obtained with the X-ray generating part and X-ray detecting part as well as the virtual X-ray generating part and the virtual X-ray detecting part locating at the same positions at the time of the imaging and the forward projection, respectively.

Effect of the Invention

According to the present invention, a differential view image in which only information on an organ in a region of interest is imaged can be provided by using a view image of sufficiently high time resolution for motions of the heart. Observation of such a differential view makes it easier for an inspector to detect an objective blood vessel or judge whether stenosis is present or not, and thus improves diagnostic ability.

BRIEF DESCRIPTION OF THE DRAWINGS

FIG. 5 shows an example of setting screen for setting creation conditions of a differential view image.

MODES FOR CARRYING OUT THE INVENTION

Hereafter, embodiments of the present invention will be explained in detail with reference to the drawings.

Figure 1:
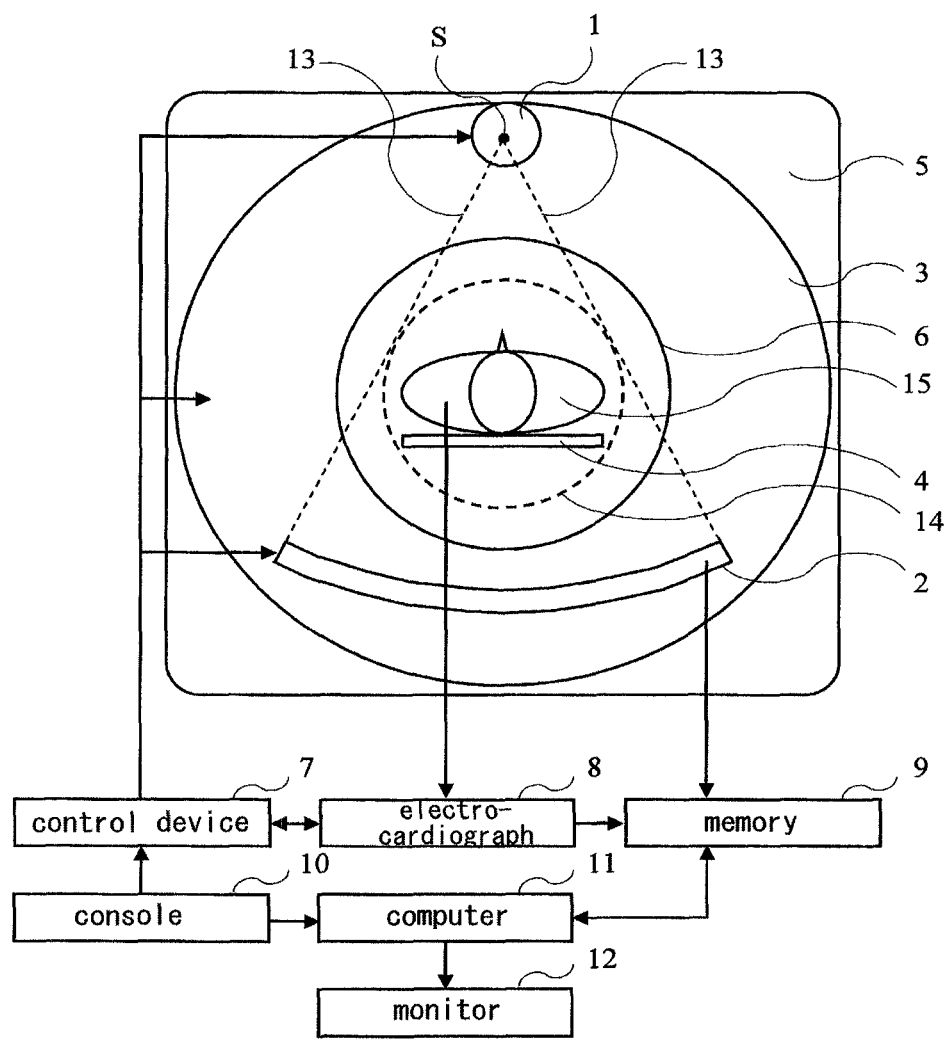
FIG. 1 is a schematic front view of an X-ray CT device according to an embodiment of the present invention.

FIG. 1 is a schematic front view of an X-ray CT device according to an embodiment of the present invention. The X-ray CT device according to this embodiment consists of an X-ray tube (X-ray generating part) 1, an X-ray detector 2, a rotating plate (turntable) 3, a top of bed 4, a gantry 5, a control device 7, an electrocardiograph 8, a memory 9, a console 10, a computer 11, a monitor 12, and so forth.

The imaging system consisting of a pair of the X-ray tube 1 and the X-ray detector 2 is fixed on the turntable 3, and these imaging system and turntable 3 as a whole are accommodated inside the gantry 5. An opening 6 is provided at the center of the gantry 5, and a subject 15 is placed around the center of the opening 6. In this embodiment, a human body is supposed as the subject 15, and measurement is performed for the subject 15 lying on the top of bed 4. As a result of revolution of the turntable 3 attained by a driving apparatus not shown in the drawing, the imaging system acquires X-ray transmission images of the subject 15 from all the radial directions. The position of the top of bed 4 can be moved along the direction perpendicular to the plane of the drawing by a driving apparatus not shown in the drawing. It is also possible to perform a known helical scan by simultaneously revolving the turntable 3 and moving the top of bed 4.

Figure 2:
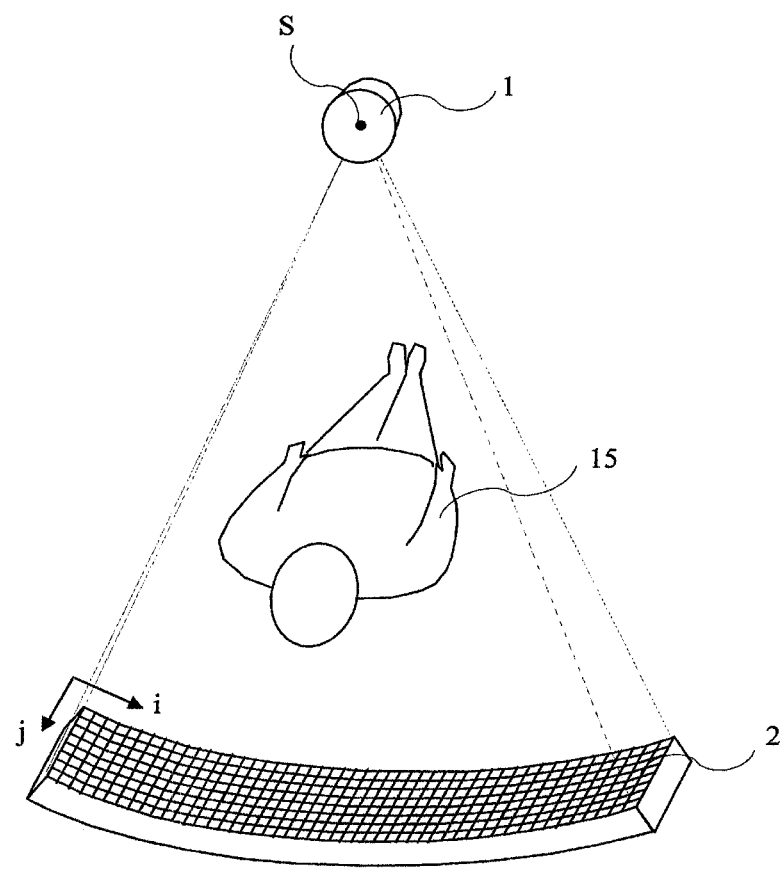
FIG. 2 is a perspective view for explaining positional relationship of an X-ray tube and an X-ray detector in the X-ray CT device of FIG. 1.

As the X-ray detector 2, a known X-ray detector consisting of a scintillator, photodiode, and so forth is used. As shown in FIG. 2, the X-ray detector 2 has a two-dimensional X-ray incidence surface consisting of many X-ray detecting elements, and the X-ray incidence surface is disposed so as to face the X-ray tube 1. These X-ray detecting elements are arranged on a circular arc along the channel direction so that they are at substantially the same distances from an X-ray generating point S of the X-ray tube 1. A part of X-rays emitted from the X-ray tube 1 penetrates the subject 15, and then detected by the X-ray detector 2. On the incidence surface of the X-ray detector 2, the X-ray detecting elements are arranged in the shape of a matrix of the channel direction (direction of i in the drawing), and the slice direction (direction of j in the drawing), and a two-dimensional X-ray transmission image, i.e., view image, of the subject 15 can be obtained therewith.

As shown in FIG. 1, the imaging field of view of the X-ray CT device corresponds to the inside of a circle 14 inscribed with the straight lines 13 connecting the X-ray generating point S and the both ends of the of X-ray detector 2 for the channel direction, and is called FOV (field of view). A CT image of the subject 15 and the top of bed 4 in the FOV is reconstructed by using a known calculation method.

Figure 3:
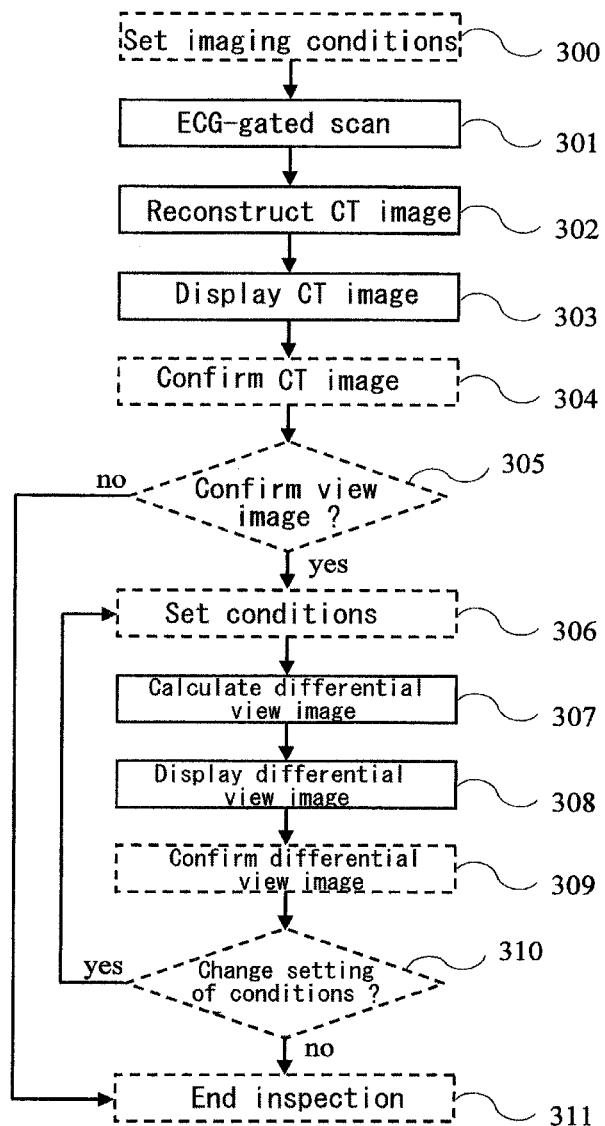
FIG. 3 is a flowchart for explaining operational procedure performed by an inspector in the electrocardiography-gated scan.

Hereafter, operations of the X-ray CT device according to this embodiment will be explained. The outline of the procedure of the electrocardiography-gated scan is shown in FIG. 3. The steps indicated with dashed lines in FIG. 3 correspond to actions performed by an inspector, and the steps indicated with solid lines correspond to operations of the X-ray CT device. The X-ray CT device of the present invention is characterized by the processings executed after the creation of CT image, i.e., the processings of the step 305 and thereafter shown in FIG. 3, and the imaging operation is the same as that of common X-ray CT devices. Hereafter, the imaging operation will be briefly explained.

First, the inspector places the subject 15 on the top of bed 4, and then sets imaging conditions from the console 10 (Step 300). Typical imaging conditions are imaging position and imaging area (range) of the subject 15, moving pitch of the top of bed 4 in the helical scan, tube voltage and tube current of the X-ray tube 1, revolving speed of the imaging system, and so forth, and these are set by using known methods.

In the case of the electrocardiography-gated scan, when the imaging conditions are inputted, it is also directed whether the retrospective scan or the prospective scan is performed.

Then, the inspector directs to start the imaging from the console 10 (Step 301). Upon receiving the direction for starting the imaging, the control device 7 starts revolution of the turntable 3. Further, the control device 7 changes the position of the top of bed 4 to place the subject 15 at an imaging position set beforehand. When the revolution of the turntable 3 reached a predetermined constant speed, the control device 7 directs the X-ray tube 1 to irradiate X-rays, and the X-ray detector 2 to detect signals to start the imaging. Data of view images outputted from the X-ray detector 2 during the imaging are successively stored in the memory 9. Upon the start of the storage of the data, the computer 11 calculates a CT image of the subject 15 by using a known reconstruction algorithm, and stores calculation results in the memory 9 (Step 302). Further, the computer 11 displays the aforementioned calculated CT image on the monitor 12 (Step 303). In the case of the helical scan, the aforementioned turntable 3 and the top of bed 4 are simultaneously rotated and moved, respectively. In this case, a series of the aforementioned processings from data acquisition to display of a CT image on the monitor 12 are successively repeated until imaging is completed for an imaging area specified beforehand.

When it is directed to perform the retrospective scan, the control device 7 directs the electrocardiograph 8 to measure an electrocardiogram of the subject 15, and measurement results of the electrocardiogram during the imaging are recorded in the memory 9. After the end of the imaging, the inspector specifies a desired cardiac time phase from the console 10. On the basis of the information in the electrocardiogram recorded in the memory 9, the computer 11 selects and reads out data of view images required for reconstruction from the memory 9 in a known manner, and reconstructs a CT image at the specified cardiac time phase.

When the prospective scan is directed, the control device 7 directs the electrocardiograph 8 to measure an electrocardiogram of the subject 15 in advance of the imaging, and the measurement results are recorded in the memory 9. The computer 11 calculates mean cycle of heartbeat and timing of imaging in a known manner on the basis of the information in the electrocardiogram recorded in the memory 9. Then, the control device 7 performs imaging with the aforementioned calculated imaging timing using a signal of the electrocardiograph 8 as a trigger, and records an acquired view image in the memory 9. The computer 11 reads the data of the view image recorded in the memory 9, and reconstructs a CT image using a known reconstruction algorithm.

The inspector examines the CT image obtained by the electrocardiography-gated scan (Step 304), and then directs display of a differential view image from the console 10, if desired. Examples of such a case include, for example, a case where the inspector cannot judge whether an object that appears to be angiostenosis on a CT image is a real lesion or a motion artifact.

When the inspector has judged that it is necessary to confirm a view image, the inspector directs display of a differential view image, and sets conditions for creating the differential view image (Step 306). When the conditions are set, on the basis of these conditions, the computer 11 selects and reads out a predetermined view image from the memory 9, reads out a CT image from the memory 9, and creates a differential view image (Step 307). The procedure for creating the differential view image will be explained in detail below. The created differential view image is displayed on the monitor 12 (Step 308).

Thus, the inspector can use the displayed differential view image for diagnosis. The inspector sees the differential view image (Step 309), and then judges whether it is necessary to change the set conditions for creating the differential view image (Step 310). When it is judged that change of the set conditions is needed, the process returns to the condition setting of Step 306. The operations of Steps 306 to 310 mentioned above are repeated until the inspector judges that further change of the set conditions is unnecessary in Step 310. When the inspector judges that change of the set conditions is unnecessary in Step 310, that examination is ended (Step 311). Further, also when it is judged that confirmation of a view image is unnecessary in Step 304, the examination is ended (Step 311).

Figure 4:
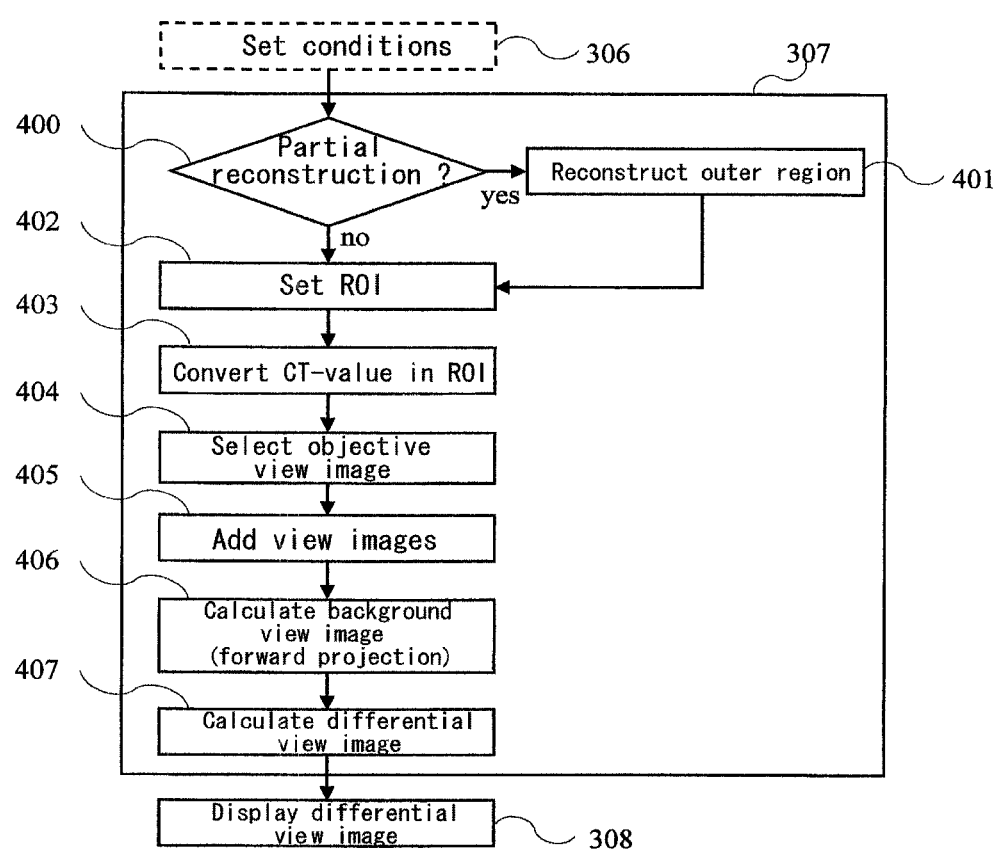
FIG. 4 shows an example of flowchart for explaining procedure for calculating a differential view image.

Hereafter, the details of the creation of a differential view image (Steps 306 and 307 mentioned above) will be explained with reference to FIGS. 4 and 5. FIG. 4 shows the details of Step 307 mentioned in FIG. 3 for creating a differential image, and FIG. 5 shows an example of setting screen displayed on the monitor 12 for setting conditions for creating a differential image.

As shown in FIG. 4, the creation of a differential image comprises setting conditions including setting of a region of interest (Step 306), processing for acquiring a CT image including the total region of the subject 15 and the top of bed 4 (Steps 400 and 401), processing for changing the region of interest (Step 402), processing for replacing CT values of pixels in the region of interest (Step 403), processing for selecting a view image used for creation of a differential view image (Step 404), processing for adding view images (Step 405), processing for creating a background view image corresponding to the selected view image using a CT image of which CT value is replaced (Step 406), processing for obtaining a difference of the selected view image and the background view image created in Step 406 and calculating a differential view image (Step 407), and displaying the differential view image (Step 308).

The setting screen shown in FIG. 5 is a screen for the inspector to set the conditions of the aforementioned processings from the console 10, and consists of a region-of-interest setting part 500, a CT value replacement setting part 501, a view image addition setting part 502, and a view image creation range setting part 503. The setting of the conditions (Step 306) is performed by using this setting screen.

In FIG. 5, the portions of small circles represent known radio buttons generally used in a GUI (graphical user interface) environment, and by clicking each button by using a known means such as a mouse, selection or no selection of each item can be directed. Further, in FIG. 5, the rectangular portions represent known text boxes generally used in a GUI environment, and numerical values can be inputted into them by using a known means such as a keyboard.

Hereafter, details of each processing will be explained.
<Condition Setting Step 306>

Setting of the conditions for creating a differential image can be performed by using the region-of-interest setting part 500, the CT value replacement setting part 501, the view image addition setting part 502, and the view image creation range setting part 503 of the setting screen shown in FIG. 5. Hereafter, setting of conditions performed with each part will be explained.
<<Setting of Region of Interest>>

Setting of a region of interest is a processing for specifying a region for which the inspector desires to obtain an image in a differential image to be finally obtained, and is performed by specifying the shape and conducting extraction or exclusion using a CT value (threshold value) on the basis of the CT image displayed on the monitor 12.

Figure 6:
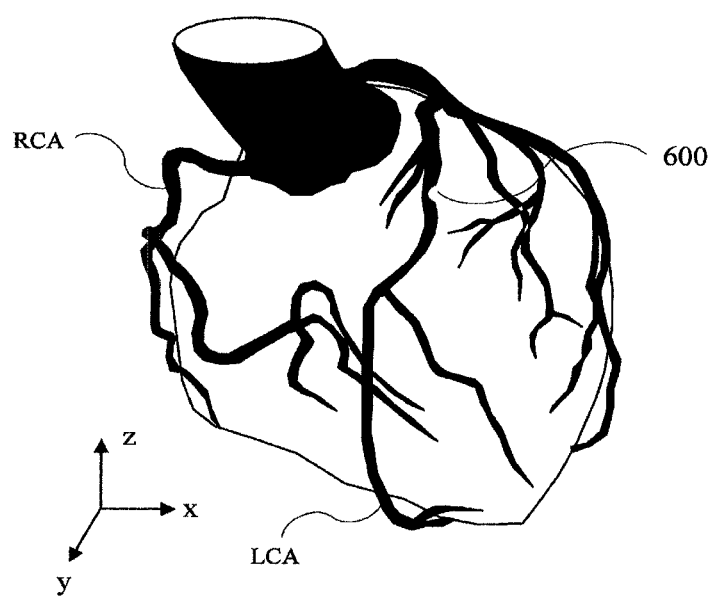
FIG. 6 shows an example of display of a CT image acquired by electrocardiography-gated scan on a monitor 12.

For this purpose, such a CT image obtained by electrocardiography-gated scan as shown in FIG. 6 is displayed on the monitor 12 along with the setting screen shown in FIG. 5. The example shown in the drawing is an example of a volume rendered image created by a known method for a CT image of an area around the heart of the subject 15, but the display scheme of a CT image is not limited to that of this example. In this example, the right coronary artery (RCA), the left coronary artery (LCA) surrounding the circumference of the heart, and so forth are imaged. These consist of images of X-ray contrast medium injected into the blood in the arteries, and they have a relatively high CT value compared with surrounding tissues. Further, in this example, a part 600 suspected to be a stenosis exists in the left coronary artery (LCA). Hereafter, explanation will be made for a case where the inspector attempts to create a differential view image of the left coronary artery (LCA), in order to investigate whether the part 600 is true angiostenosis or a motion artifact. For this purpose, the inspector sets a part desired to be imaged in the differential view image using the region-of-interest setting part 500 shown in FIG. 5.

The inspector first clicks a radio button to choose the geometric shape of the region of interest. On the screen shown in the drawing, as the geometric shape, whole region, spherical shape, and box shape are provided. However, the selectable shape is not limited to these, and arbitrary shapes such as cylindrical shape and spheroidal shape may be provided. For example, when the spherical shape is chosen, it becomes possible to input the center coordinates thereof (xo, yo, zo) and the diameter d into the text boxes. When a box shape is chosen, it becomes possible to input the center coordinates thereof (xo, yo, zo) and the sizes (wx, wy, wz) into the text boxes. Numerical values for the region of interest can be directly inputted into the text boxes on the setting screen shown in FIG. 5, or they can also be changed by dragging the center coordinates O or the outer frame of the region 600 by using a mouse or the like on the volume rendered image shown in FIG. 6. In addition, when the whole region is specified in the region-of-interest setting part 500 at the time of the setting of the geometric shape, the entire region of the CT image is specified as the region of interest.

Figure 7:
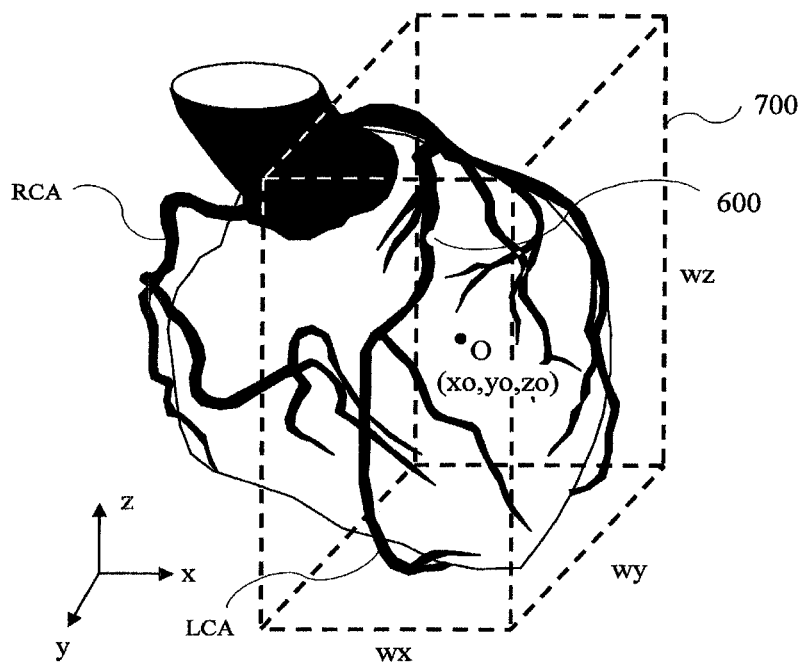
FIG. 7 shows an example of display of a box-shaped region of interest.
Figure 8:
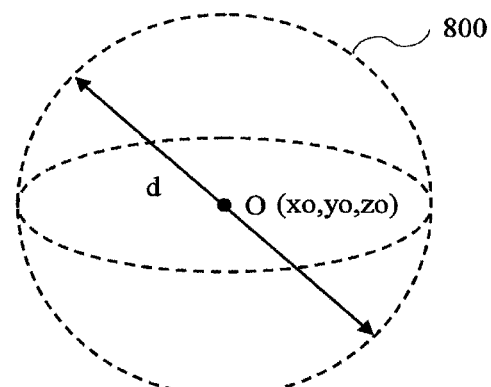
FIG. 8 shows an example of display of a spherical-shaped region of interest.

FIG. 7 shows an example of display of a box-shaped region of interest. According to the inputted center coordinates (xo, yo, zo) and the sizes (wx, wy, wz), a corresponding region is displayed as an overlapping image on the volume rendered image. In this example, the box-shaped region of interest 700 is set near the left coronary artery (LCA). FIG. 8 shows an example of display of a spherical-shaped region of interest 800. As in the case of the box-shaped region of interest, according to the set values of the center coordinates (xo, yo, zo) and the diameter d inputted into the text boxes, a corresponding region is displayed as an overlapping image on the volume rendered image.

Then, the inspector specifies whether threshold extraction is further performed in the region of interest set in the aforementioned process or not by using a radio button. When no extraction is chosen, the whole region specified in the aforementioned setting of the geometrical shape is specified as the region of interest. In this case, an X-ray transmission image of the whole region of interest will be imaged in the differential view image.

The threshold extraction is a processing for extracting a part especially desired to be imaged in the differential view image to be finally created from the region specified with the shape, and it is performed when use of extraction is chosen, and a range of CT value is specified in the text boxes.

As exemplified in FIG. 7, when a box-shaped region of interest including the left coronary artery (LCA) is specified in order to diagnose existence of a stenosis in the left coronary artery (LCA), a part of the heart existing around the left coronary artery (LCA) is also included in the region of interest. Therefore, if a differential view image is created for this box-shaped region as the region of interest, the heart, other tissues etc. are also imaged in the differential view image, in addition to the left coronary artery (LCA) that should be essentially observed, and the contrast of the blood vessel moiety to be observed is reduced. In such a case, by setting an appropriate threshold value using the fact that the CT value in the portion of the left coronary artery (LCA) into which the contrast medium flowed is higher than that of the circumference, only that portion can be extracted. The information on tissues around the left coronary artery (LCA) can be thereby removed from the differential view image to improve the contrast of the blood vessel moiety.

Figure 9:
FIG. 9 shows an example of a region of interest narrowed down by threshold extraction.

Specifically, the inspector chooses use of threshold extraction on the setting screen, and sets the threshold value of the CT value in the text box to narrow down the region of interest. Responding to the above operation, the computer 11 extracts only voxels of a value existing in the set CT value range from the aforementioned region of interest, and sets the region of them again as a new region of interest. FIG. 9 shows an example of the region of interest narrowed down by the threshold extraction. In this example, the region of interest is narrowed down to only the left coronary artery (LCA).

Size of the region extracted by using the threshold value can be expanded or reduced, as required. For example, if the threshold value range for the threshold extraction is set to be relatively narrow in order to improve accuracy of extraction of a blood vessel moiety, a region essentially desired to be extracted (region of relatively high CT values) may remain in a region of no interest near the extracted region, and may not be extracted. Such a region omitted from the extraction may be imaged in the background view image by the forward projection calculation described later, and may generate a false image in the differential view image, as a result.

Figure 10:
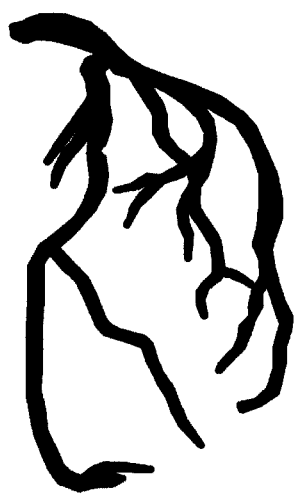
FIG. 10 shows an example of the region of interest shown in FIG. 9 expanded by region expansion.

Such a false image can be prevented by expanding the region extracted by the threshold extraction. Specifically, if a positive value is inputted in the text box of the region expanding range d of the region-of-interest setting part 500, the extracted region can be expanded outward by the specified distance. FIG. 10 shows an example of an expanded region obtained by expanding the region of interest shown in FIG. 9. Conversely, it is also possible to input a negative value in the text box of the region expanding range d to reduce the region of interest.

Although the processing of setting the region of interest by specifying the geometrical shape and then extracting the region of interest by the threshold extraction was explained above, instead of such region extraction using a threshold value, or together with the threshold extraction, a region to be excluded from the region of interest may also be specified with CT values.

Specifically, whether the above exclusion is performed or not is selected by using the radio button, and when the exclusion is performed, a range of CT value of a region desired to be excluded is specified in the text boxes. This function can be used for, for example, such a case where the inspector wants to exclude only the part of the heart from the region of interest.

Although the setting of the region of interest is performed by using the region-of-interest setting part 500 as explained above, the items set by using the region-of-interest setting part 500 are not limited to only the specific examples explained above, and the inspector can variously change the aforementioned setting according to use or purpose to create a desired differential view image. For example, if the whole region specified with a geometric shape is specified as the region of interest, there is brought a disadvantage of reduced contrast of blood vessels imaged in the differential view image, but is obtained an advantage that there can be obtained a differential view image relatively stable for motions of the subject. Further, if a region extracted by using a threshold is specified as the region of interest, there is brought a disadvantage that there is obtained a differential view image relatively unstable for motions of the subject, but is obtained an advantage that contrast of blood vessels imaged in the differential view image is improved.

<<Setting of CT Value Replacement>>

CT value replacement is a processing for replacing data values of the region of interest of the CT image used for creation of a background view image with predetermined values, so that, when a background view image is subtracted from a view image, only the region of interest is imaged. According to this embodiment, replacement with a constant value or interpolated value, or no replacement can be selected by using the radio button in the CT value replacement setting part 501.

When replacement with a constant value is selected, the inspector sets the value in the text box. In this case, the pixel values of all the pixels included in the region of interest set by using the region-of-interest setting part 500 are replaced with the set value in Step 403 mentioned in FIG. 4. Such replacement with a constant value is preferred for the case where a region of interest having a relatively large volume such as a whole geometric region is specified, and there is provided an advantage that a differential view image showing reduced density unevenness can be obtained.

Figure 11A:
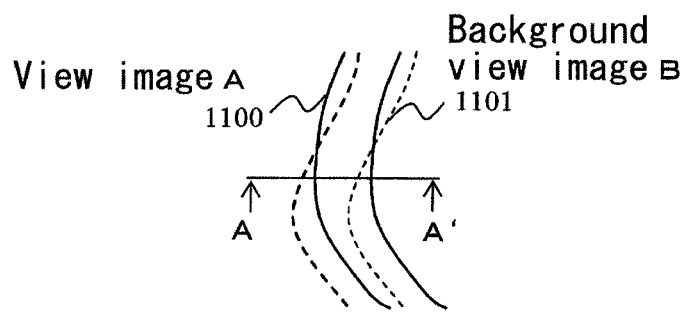
FIGS. 11A and 11B are diagrams for explaining unevenness of density generated in a differential image when a narrow region is set.
Figure 11B:
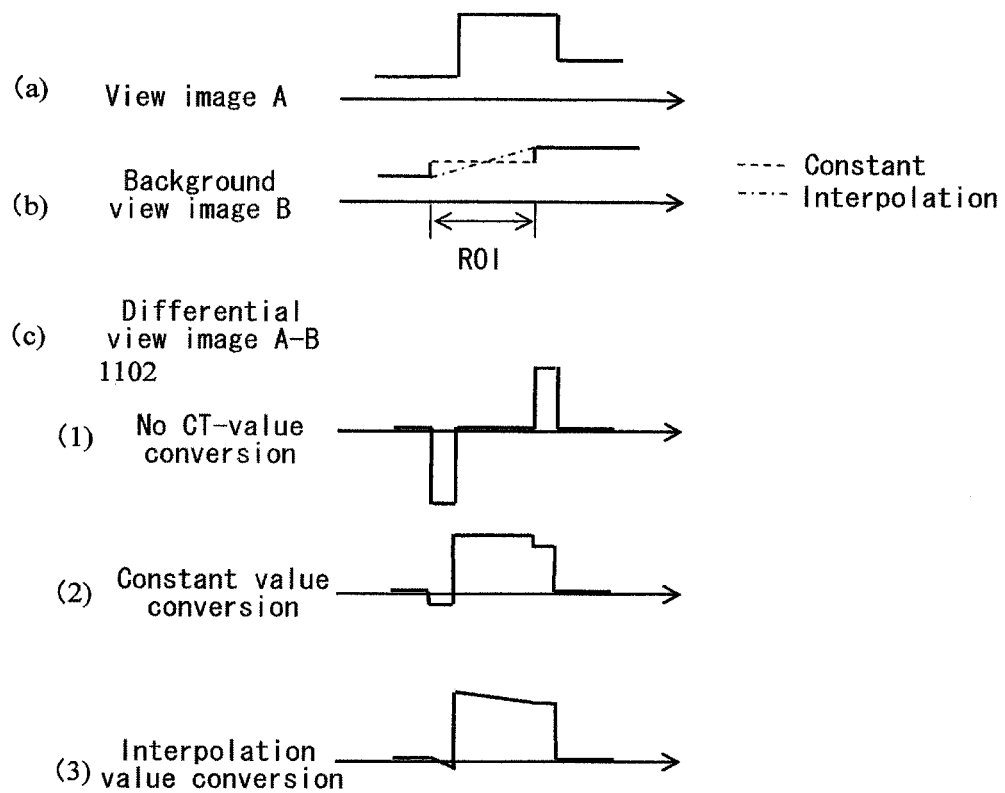

When replacement with an interpolated value is chosen, the CT values in the region of interest are replaced with a value interpolated from a value of a neighboring region of no interest. The replacement with an interpolated value is preferred for the case where a region of interest having a relatively small volume such as a blood vessel moiety extracted with a threshold value is specified. The effect of the replacement of the CT value will be explained with reference to FIG. 11. FIG. 11A shows relationship between a view image A of a blood vessel 1100 and a background view image B, FIG. 11B, (a) and (b) show density profiles of the view image A and the background view image B along the line A-A' drawn in FIG. 11A, respectively, and FIG. 11B, (c) shows differential view images. In FIG. 11B, (b), the broken line represents the result of replacement with a constant value, and the alternate long and short dash line represents the result of replacement with an interpolated value. As shown in FIG. 11A, if discrepancy is generated between the position of the blood vessel 1100 in the view image and the position of the blood vessel 1101 in the background view image accompanied with a motion of the subject, and a difference is acquired for the region of interest in which CT values are replaced with a constant value, significant density unevenness is generated in the differential view image 1102 as shown in FIG. 11B, (c), (2). When the values are replaced with an interpolated value instead of a constant value, such density unevenness can be eliminated as shown in FIG. 11B, (c), (3).

When no replacement is chosen, CT values in the region of interest are not replaced. This is equivalent to the case where the region of interest is not specified. In this case, as shown in FIG. 11B, (c), (1), information on the positional discrepancy induced by a motion of the subject is imaged in the differential view image. Therefore, the inspector can estimate magnitude of the motion by referring to the differential view image.

The items to be set in the CT value replacement setting part 501 are also not limited to those exemplified above, and the inspector can variously change the setting according to use or purpose to create a desired differential view image.

<<View Image Addition Setting>>

Addition of view images is performed for improving S/N of view image. That is, in the X-ray CT device according to this embodiment, the number of times of imaging in one revolution of the imaging system is typically about 1000, and therefore when the revolving speed is 0.35 [second/revolution], exposure time of each view image is 0.35 [ms]. Since the exposure time of each view image is extremely short as described above, degradation of S/N due to the quantum noise of X-ray or circuit noise of X-ray detector 2 poses a problem. By adding several view images acquired in time series, S/N can be improved.

In the view image addition setting part 502, conditions for the addition processing executed in Step 405 are set. Specifically, number M of images to be added or exposure time T is inputted into the text box. It is also possible to determine the number of images to be added on the basis of amount of noises, which is specified by the inspector, instead of directly inputting the number M of images to be added. Further, as for the weighting function used for the addition, for example, that of rectangular type or triangular type can be selected by using a radio button.

<<View Image Creation Range Setting>>

The inspector specifies angle range and angle step of a differential view image to be created in the text boxes of the view image creation range setting part 503 shown in FIG. 5. In the example shown in FIG. 5, the angle range is specified as 0 to 360 degrees, and the angle step is specified as 10 degrees. Therefore, a differential view image is created for every 10 degrees from a revolution angle of zero degree of the imaging system, and 37 differential view images in total are created up to 360 degrees.

<Step 307>

After the conditions for creating a differential image are set as described above, Step 307 of creating a differential image is started. Hereafter, the processings of Step 307 will be explained in detail.

<<Processings 400 and 401 for Acquiring CT Image Covering Whole Region>>

These processings are processings for making the imaging area of the view image as actually measured data and the reconstruction region of the CT image for creating the background view image coincide, and they become necessary when the CT images stored in the memory 9 are partial reconstructed images obtained by reconstructing a part of the imaging region. These processings will be explained in detail with reference to FIGS. 12 to 14.

Figure 12:
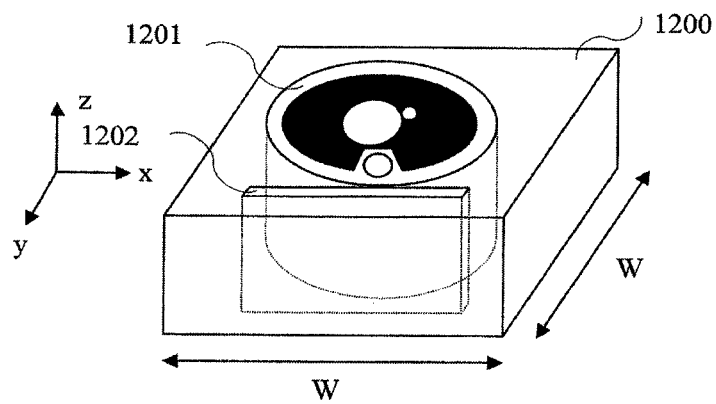
FIG. 12 is a drawing for explaining a maximum reconstruction region 1200.
Figure 13:
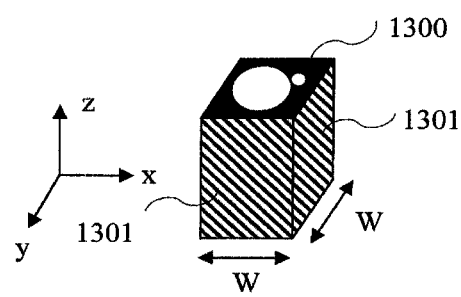
FIG. 13 is a drawing for explaining a partial reconstruction region 1300.
Figure 14:
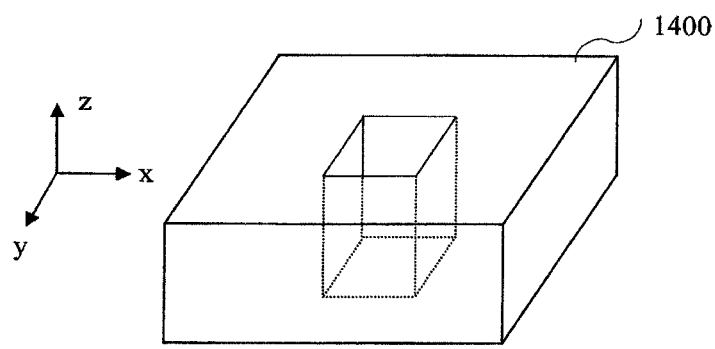
FIG. 14 is a drawing for explaining an outer reconstruction region 1400.

The X-ray CT device has a predetermined FOV, and as shown in FIG. 12, the maximum reconstruction region thereof is a region 1200 of which size W for the x- and y-directions defines FOV mentioned above. Therefore, the maximum reconstruction region 1200 has a sufficiently large size for the xy-plane direction, and completely includes a subject region 1201 and a top of bed region 1202. The view image (projection image) used for creating a CT image is an image in which all the objects existing in the region 1200 are imaged. That is, the imaging region of the view image corresponds to the maximum reconstruction region. However, in the electrocardiography-gated scan etc., only a partial region such as the heart is partially reconstructed, and a CT image of high spatial resolution is acquired in many cases. In such a case, as shown in FIG. 13, neither a circumferential part of the subject region 1201 nor the top of bed region 1202 is included in the partial reconstruction region 1300. Therefore, if forward projection is performed for a CT image of such a partial reconstruction region 1300, and subtraction from the view image is performed to create a differential view image, information on the aforementioned top of bed etc. is imaged in the differential view image. These processings are performed in order to prevent such a problem as mentioned above.

For such a purpose, the computer 11 first judges whether a CT image already calculated and stored in the memory 9 is reconstruction of a part or not (Step 400). As for the judgment on whether the CT image is reconstruction of a part or not, for example, it is examined whether a pixel having a CT value significantly deviated from the CT value of air, −1000 [HU], exists in an end surface 1301 of the CT image, and when such a pixel exists, it is judged that the CT image is a partial reconstruction image. When it is judged that the CT image is not a partial reconstruction image in Step 400, the process moves to the next processing (Step 402). When it is judged that the CT image is a partial reconstruction image, in addition to the already existing CT image of the partial reconstruction region 1300, a CT image is also calculated for an external reconstruction region 1400 shown in FIG. 14 (Step 401). The external reconstruction region referred to here is a region of the maximum reconstruction region 1200 except for the partial reconstruction region 1300. Since view image data of the maximum reconstruction region are stored in the memory 9, the CT image of the external reconstruction region 1400 is calculated by using them. Then, the process moves to the following Step 402. The forward projection processing (Step 406) explained later is performed for both the partial reconstruction region and the external reconstruction region, and the total of the both is used as a background view image.

<<Processing 402 for Changing Region of Interest>>

As already explained, the region of interest is set by specifying position or shape thereof on a CT image, or performing the threshold extraction in the condition setting step, Step 306. This processing is executed only when the setting of the region expanding range d is not 0 in the region-of-interest setting part 500 shown in FIG. 5.

Figure 15:
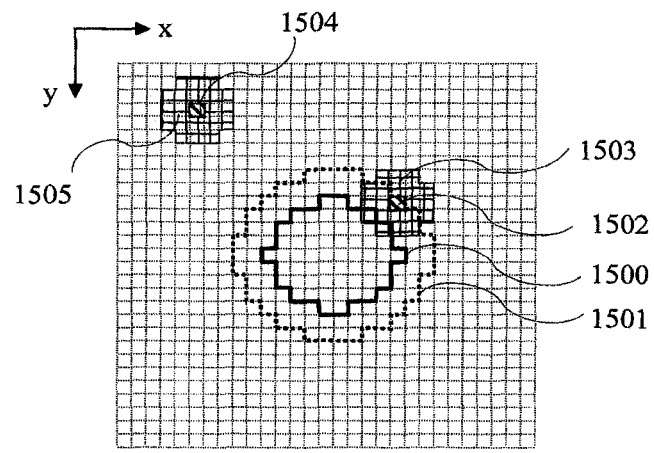
FIG. 15 is a diagram for explaining a region expanding method for a region of interest in a CT image.

A method by which the computer 11 expands or reduces the region of interest on the basis of the numerical value inputted in the text box of the region expanding range d will be explained with reference to FIG. 15. It is assumed that, in FIG. 15, a region of interest 1500 is extracted by the threshold extraction calculation already explained above.

The computer 11 judges whether each of all pixels in a region specified with a geometrical shape is within the range of the region expanding range d from the region of interest 1500 or not, that is, belongs to a region neighboring the region of interest. For this purpose, a region 1503 of pixels within the range of a radius d from a certain pixel 1502 as the center is extracted. Then, it is examined whether the region 1503 has a pixel also belonging to the region of interest 1500, and when there is such a pixel, it is judged that the pixel 1502 belongs to the neighboring region. In the example shown in FIG. 15, the region 1503 around the pixel 1502 overlaps with the region 1500, and therefore belongs to the neighboring region. On the other hand, the region 1505 around a pixel 1504 does not overlap with the region of interest 1500, and therefore it is judged not to belong to the neighboring region. As a result of the aforementioned judgment for all the pixels in the region of no interest on the xy plane, the region of interest 1500 is expanded to the region 1501 in this example. The same processing is performed for all the xy planes.

When the region expending range d is a positive value, the aforementioned expansion processing is performed, but when d is a negative value, a reducing processing is performed. In the latter case, it is judged whether a pixel within the range of radius −d from the pixel as the center also belongs to the region of no interest for all the pixels within the inside of the region of interest 1500. When a pixel within a predetermined range from a certain pixel is also belongs to the region of no interest, the latter pixel is excluded from the region of interest. By performing such processing, the region can also be reduced.

<<Processing 403 for Replacing CT Value of Region of Interest>>

After the region of interest is decided by the condition setting 306 and the processing 402 mentioned above, CT values in the decided region of interest on the CT image are replaced with a value specified by the CT value replacement setting part 501. When a constant value is chosen and a value thereof is inputted, all the values of the pixels in the region of interest are replaced with that value. When interpolation is chosen, an interpolated value is calculated for each pixel in the region of interest by the method described below, and the value of each pixel is replaced with that value.

Figure 16:
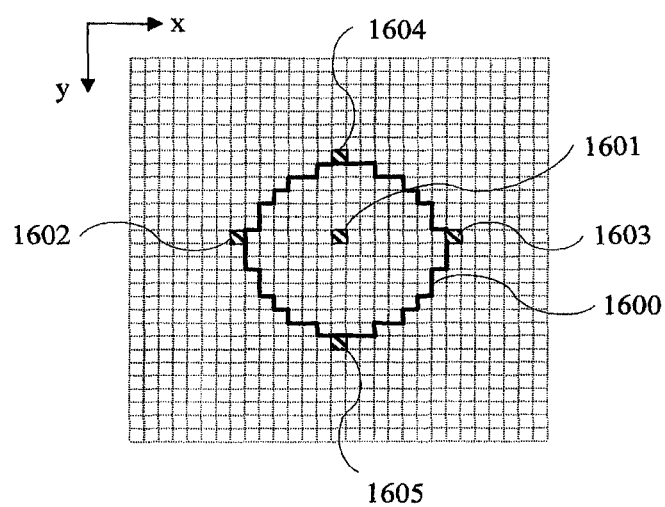
FIG. 16 is a diagram for explaining a method for interpolating a CT value in a region of interest in a CT image.

An example of the calculation method for the case where interpolation is chosen will be explained with reference to FIG. 16. For example, when a CT value of a pixel 1601 existing in the inside of a region of interest 1600 is interpolated, first, two pixels 1602 and 1603 having the same coordinate for the y-direction as that of the pixel 1601 and most close to the pixel 1601 are determined among the pixels in the region of no interest, and an interpolated value of the pixel 1601 for the x-direction is calculated by linear interpolation using the values of these two pixels. In the same manner, from values of two pixels 1604 and 1605 having the same coordinate for the x-direction as that of the pixel 1601 and most close to the pixel 1601 among the pixels in the region of no interest, an interpolated value of the pixel 1601 for the y-direction is calculated. Finally, the aforementioned interpolated values for the x-direction and the y-direction are averaged, and the average is used as an interpolated value of the pixel 1601. The above processing is performed for all the pixels existing in the inside of the region of interest 1600.

By using such an interpolated value as a value for replacing a CT value of the region of interest 1600 as described above, density unevenness can be made small even when the positional discrepancy is generated by motions of a subject. However, for a region of interest having a relatively large volume, unevenness of density may be generated in a differential view image due to error of the interpolation calculation. In such a case, it is preferable to use a constant value.

When no replacement is chosen in the CT value replacement setting part 501, the replacement of the CT value in the region of interest is not performed. That is, the processing of Step 403 is omitted.

The CT image subjected to the replacement processing is used for calculation of a background view image in Step 406.

<<Processing 404 for Choosing View Image Used for Creation of Differential View Image>>

Figures 17, 18:
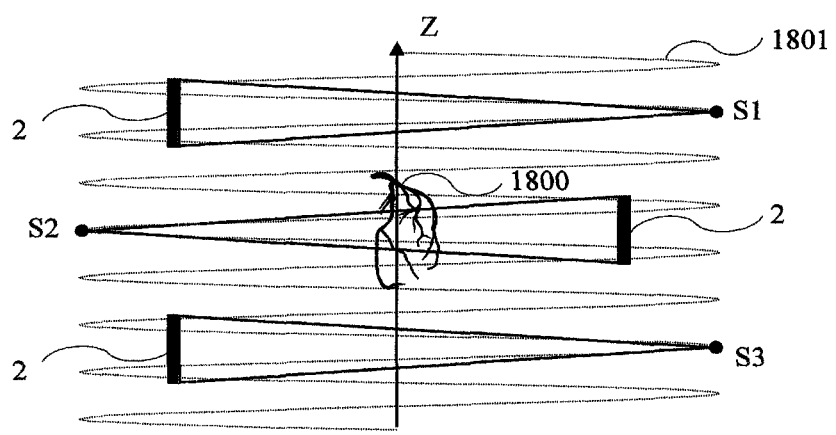
FIG. 17 shows a table for explaining a method for selecting a view image with which a differential view image is created.
FIG. 18 is a drawing for explaining a method for selecting a view image in which a region of interest 1800 is included in a field of view.

In this processing, from a plurality of view images (actually measured view image) stored in the memory 9, a view image used for creation of a differential view image is chosen. An example of a method for selecting a view image for use in creation of a differential view image is shown in FIG. 17. In this embodiment, the view image for use in the creation is chosen as a view image satisfying all the following three conditions: (Condition 1) it is used for reconstruction of a CT image, (Condition 2) it is included in the range specified by the view image creation range setting part 503 shown in FIG. 5, and (Condition 3) a region of interest is included in a field of view.

(Conditions 1) is for excluding a view image not used for creation of a CT image in the retrospective reconstruction from those for use in creation of a differential view image. Degradation of image quality of the differential view image resulting from difference of the cardiac time phase can be thereby prevented.

(Conditions 3) is a condition for omitting calculation of an unnecessary differential view image, and the calculation is thereby accelerated.

A method for choosing a view image in which a region of interest 1800 is included in a field of view according to Condition 3 will be explained with reference to FIG. 18. In FIG. 18, the z-axis represents the revolving axis of the imaging system, and the X-ray generating point shall move on a spiral orbit 1801 with revolution. In this case, when the X-ray generating point exists at, for example, S1 or S3, the region of interest 1800 is not included in the imaging field of view, and therefore a view image obtained at this time does not include information on the subject desired by the inspector. On the other hand, when the X-ray generating point exists at S2, the region of interest 1800 is included in the field of view, and information on the subject desired by the inspector is highly possibly included in a view image. Therefore, it is judged beforehand whether the region of interest 1800 is included in the field of view of each acquired view image.

The judgment is attained by, for example, judging whether lines connecting the X-ray generating point S and all the pixels in the inside of the region of interest 1800 are included in the field of view of the X-ray detector 2. When at least one pixel in the region of interest 1800 is included in the field of view for a certain X-ray generating point S, a view image obtained with that position of the X-ray generating point is chosen as a view image included in an imaging field of view.

The order of the judgments for judging whether a view image satisfies (Condition 1) to (Condition 3) mentioned above for a plurality of view images is not particularly limited. However, if acquired view images satisfying both (Condition 1) and (Condition 2) are chosen as candidates for the judgment for (Condition 3) prior to that judgment, the calculation time can be further shortened.

<<Processing 405 for Addition of View Images>>

In this processing, an addition processing is performed for the view images chosen by the aforementioned selection processing 404 with the conditions set in the view image addition setting part 502 shown in FIG. 5.

As for the number of view images to be added, when the number of view images to be added is specified in the view image addition setting part 502, view images of that number are used, and when the exposure time T is specified, the number M of view images to be added is calculated in accordance with the following equation (1).

[Equation 1]

$$M = TK/S \quad (1)$$

In the equation, T represents a specified exposure time, K represents a number of view images measured per one revolution, and S represents a time required for one revolution. For example, if T=3.5 [ms], K=1000, and S=0.35 [S], the number M of view images to be added calculated to be 10. In this case, if a view image obtained by n-th view image acquisition is represented as Pn(i,j), an added image Qn(i,j) obtained from M of view images including Pn(i,j) as the center is calculated in accordance with the following equation (2) or (3).

[Equation 2]

$$Q_n(i, j) = \sum_{k=-(M-1)/2}^{(M-1)/2} W_k P_{n+k}(i, j) \quad (2)$$

(If M is an odd number.)

$$Q_n(i, j) = \sum_{k=-(M/2)+1}^{M/2} W_k P_{n+k}(i, j) \quad (3)$$

(If M is an even number.)

In the equations, i and j represent positions of an X-ray detecting element for the channel direction and the slice direction, respectively. Further, Wk is a weighting function for integration in each view image. When a rectangular shape is chosen, the weighting function is Wk=1/M, and the same weight is integrated in each projection. Further, when a triangular shape is chosen, weight is represented by the following equation (4) or (5).

[Equation 3]

$$W_k = \frac{2}{M+1}\left(1 - \frac{2}{M+1}|k|\right) \quad (4)$$

If M is an odd number.

$$W_k = \frac{2(M+1)}{M(M+2)}\left(1 - \frac{2}{M+1}\left|k - \frac{1}{2}\right|\right) \quad (5)$$

If M is an even number.

In the case of the equation (4), the largest weight is integrated on Pn(i,j) as the center view image, and a smaller weight is integrated on a view image remoter from Pn(i,j). Therefore, there is provided an advantage that blur of image due to addition of images can be reduced. In the case of the equation (5), change of the weight is represented by a trapezoid, in which the weight becomes the maximum (height) at two center view images Pn(i,j) and Pn+1(i,j), and a smaller weight is integrated on a view image remoter from them. However, the weighting function is not limited to these examples, and for example, a weighting function for normal distribution type weighting may also be used.

<<Processing 406 for Calculating Background View Image>>

In this processing, a background view image corresponding to the view image chosen in Step 404 is calculated by using a CT image subjected to the CT value replacement processing in Step 403. The method for calculating a background view image will be explained with reference to FIGS. 19 and 20.

Figure 19:
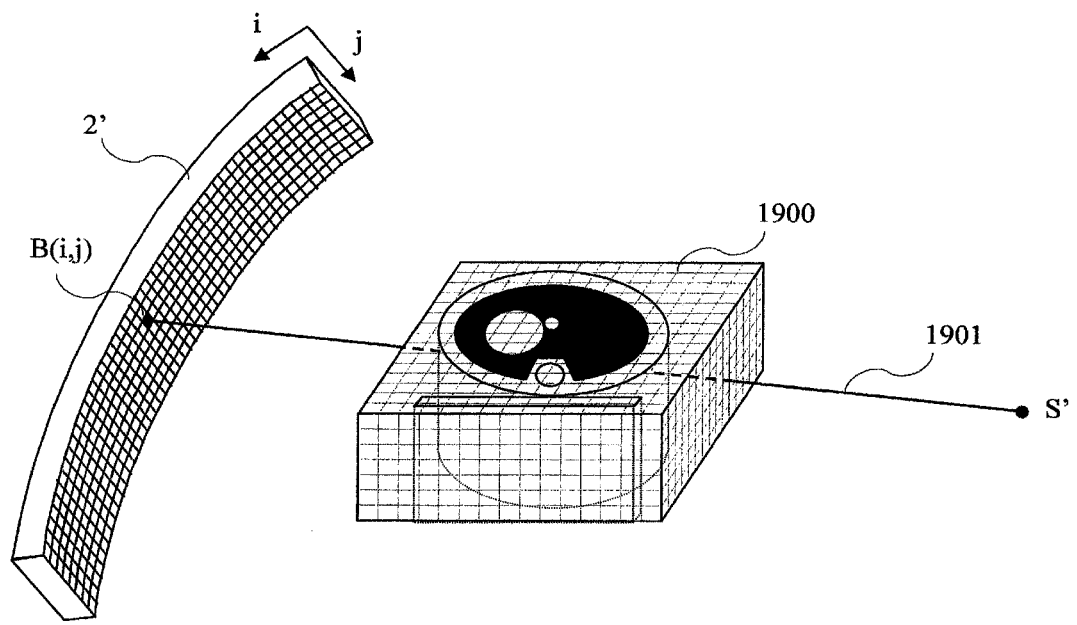
FIG. 19 is a drawing for explaining a method for calculating a background view image.

FIG. 19 is a drawing for explaining the method for calculating a background view image. For the creation of a background view image, a known technique generally called forward projection is used. In the forward projection, data values of CT image 1900 are linearly integrated on a straight line 1901 connecting the X-ray generating point S and a device B(i,j) on the X-ray detector 2, and the results are used as projection data. The X-ray generating point S' and the X-ray detector 2' used for this calculation correspond to the X-ray generating point S and the X-ray detector 2 at the positions at which the view images for the subtraction are acquired, which are virtually reproduced on a computer. The aforementioned line integral is performed for all the devices B(i,j) on the X-ray detector 2', and the obtained image data are used as a background view image. In this specification, a background view image corresponding to a view image refers to a background view image created with the same positions of the X-ray generating point S' and the X-ray detector 2' as those of the X-ray generating point S and the X-ray detector 2 used at the time of acquiring the view image.

When an external reconstruction region is created in Step 401, calculation of the forward projection mentioned above is performed for both the partial reconstruction region and the external reconstruction region, and added values of the obtained image data are used as a background view image. Further, when addition of view images is performed in Step 405, a corresponding background view image can be calculated for all the view images used for the addition, but a corresponding background view image may be calculated for a part of view images, which can shorten the calculation time. For example, when odd number-th view images are added, a background view image may be calculated only for the center view image, or when even number-th view images are added, background view images may be calculated for the two center view images, and averaged.

Figure 20:
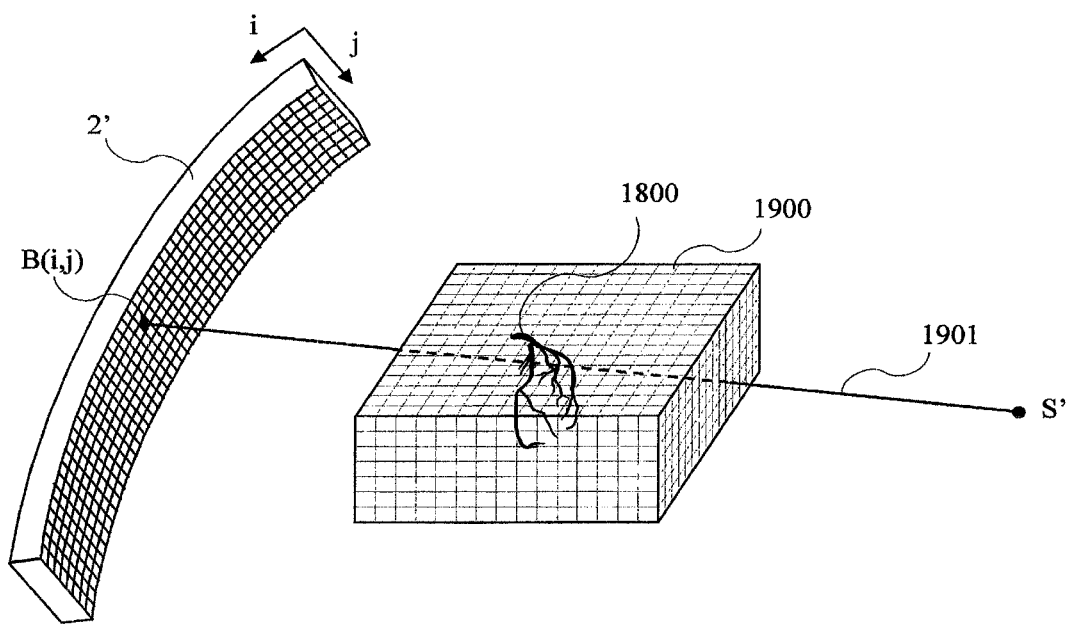
FIG. 20 is a drawing for explaining a method for calculating a background view image at high speed.

Further, since creation of a background view image by forward projection generally takes much calculation time, it is also possible to limit the beam path for which line integral is performed to a beam path 1901 passing through the region of interest 1800 for creation of one background view image, as shown in FIG. 20, to accelerate the calculation of the background view image. In this case, pixels not having data are generated in the background view image, and data values of these pixels are set to be 0 at the time of creation of a differential view image. Since the beam paths for which line integral should be performed are markedly decreased by the above limitation, a differential view image can be created at high speed.

<<Processing 407 of Calculating Differential View Image>>

In this processing, subtraction is performed between the added view image created in Step 406 and a corresponding background view image. When the view image creation range is set to be 0 to 360 degrees and the angle step is set to be 10 degrees in the view image creation range setting part 503, a differential view image is created for all the corresponding 37 view images.

<Step 308 of Displaying Differential View Image>

The differential view image created through the process of the processings 400 to 407 described above is finally displayed on the monitor 12.

Figure 21:
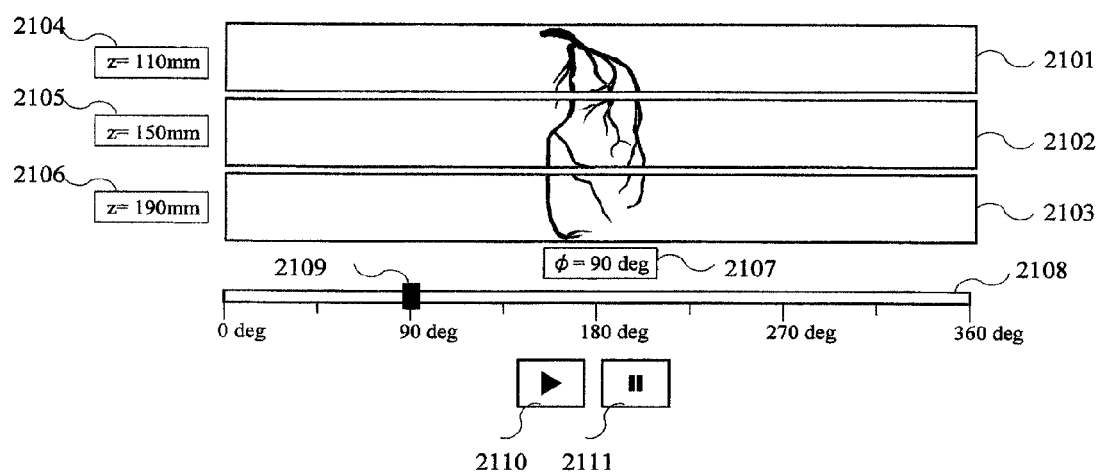
FIG. 21 shows an example of display of a differential view image on a monitor 12.

An example of display of a differential view image on the monitor 12 is shown in FIG. 21. According to this embodiment, a differential view image is created only for a view image in which the region of interest is included in the field of view, and therefore a differential view image including the region of interest is displayed. Further, when helical scan is performed, a plurality of such differential view images are usually obtained for the same projection angle direction. These are simultaneously displayed on the same screen. In the example shown in FIG. 21, three differential view images 2101 to 2103 are simultaneously displayed. In this case, the differential view images are projected from the X-ray generating point at different positions for the z-direction, respectively, and therefore the image of the subject becomes discontinuous and is separated in the differential view images. However, there is provided an advantage that, by simultaneously displaying them, it becomes easier for the inspector to understand the overall structures such as running of blood vessels.

Further, in the example of the display shown in FIG. 21, positions 2104 to 2106 of the X-ray generating point for the z-axis direction at the time of imaging of the differential view images are displayed on the display screen. An angle position 2107 of the X-ray generating point is also displayed. This angle position is also reflected in position of a cursor 2109 on an angle display bar 2108. When it is specified that a plurality of differential view images should be created for an angle direction in the view image creation range setting part 503 shown in FIG. 5, they can be displayed as an animation by clicking a replay button 2110 by using a known means such as a mouse. Further, by clicking a pause button 2111, the animation can be stopped to display a still image at an arbitrary angle position. Furthermore, by dragging the cursor 2109, the angle position can also be arbitrarily changed. The inspector can variously change the angle position of the differential view image by utilizing the aforementioned function, and can use the obtained information for diagnosis.

The scheme of the display is not limited to that shown in FIG. 21, and may be variously changed. For example, a differential view image may be displayed together with a view image before the subtraction, or together with a CT image.

One embodiment of the operation of the image processing part (computer 11) of the X-ray CT device of the present invention was explained above with reference to the flowchart of FIG. 4 and the condition setting screen shown in FIG. 5. However, the basic function of the image processing part according to the present invention is to create a differential image from a view image as an actually measured X-ray transmission image and a background view image as a pseudo X-ray transmission image created from a CT image in which CT values are replaced for a region of interest, and display it, as shown in FIG. 3, and each of the processings shown in FIG. 4 may be omitted or changed, or the order of them may be changed, as required.

Figure 22:
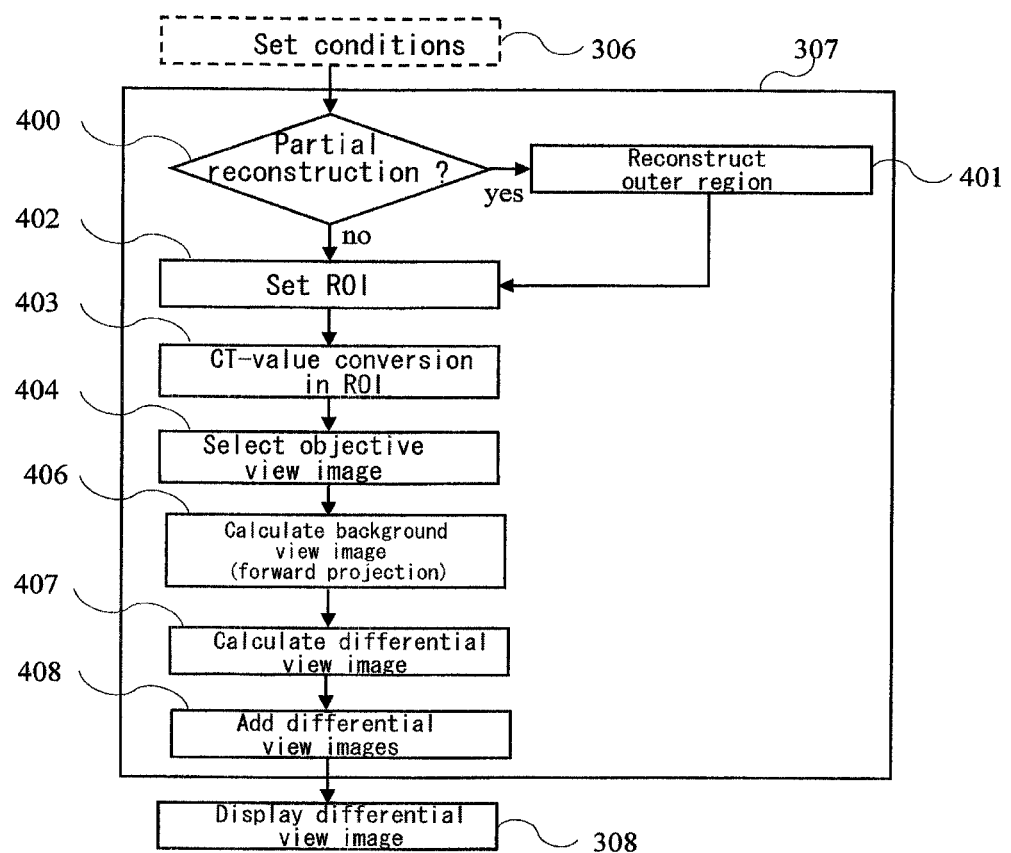
FIG. 22 shows another example of flowchart for explaining procedure of calculating a differential view image.

An embodiment in which the processing of the image processing part is changed is shown in FIG. 22. In the processing shown in FIG. 22, processings of Steps 400 to 404 are exactly the same as those of Steps 400 to 404 shown in FIG. 4, and therefore explanations thereof are omitted. This embodiment is different from the above embodiment in that addition processing of the view images selected in Step 404 is not performed, but differential view images with respect to background view images are added. Conditions for the addition of the differential view images can be set in the view image addition setting part 502 shown in FIG. 5 as in the aforementioned embodiment.

That is, after a view image used for creating a differential view image is chosen in Step 404, a background view image corresponding to the selected view image is created in Step 406. When a numerical value larger than 1 is set as the number M of images to be added in the view image addition setting part 502 shown in FIG. 5, for example, M of view images including one view image selected on the basis of the angle for the circumferential direction as the center view image and view images before and after the center view are selected in Step 404. In Step 406, M of background view images corresponding to M of the selected view images are calculated.

In Step 407, subtraction is performed between an actually measured view image and a background view image created from a CT image, and M of differential view images are obtained for one selected view image. Then, in Step 408, M of the differential view images are added. The addition can be performed by using a weighting function specified in the view image addition setting part 502 shown in FIG. 5 according to the equation (2) or (3) mentioned above.

The differential view image obtained by the addition is displayed in the same manner as that of the aforementioned embodiment (Step 308).

Although several embodiments of the X-ray CT device of the present invention were explained above, the present invention is of course not limited to the aforementioned embodiments, and can be variously embodied without departing from the spirit of the present invention. For example, the present invention can also be applied to a cone beam CT device having a C-shaped arm.

If the X-ray CT device of the present invention is used, an undesired background image can be created by forward projection calculation of a CT image for a view image obtained in an imaging process of X-ray CT, and can be removed from the view image. Display contrast of the aforementioned view image can be thereby markedly improved. Moreover, the view image has sufficient time resolution even for organs showing quick motions such as coronary artery, and therefore even for a pathological lesion for which distinction from motion artifacts is difficult only with conventional CT images, additional information for assisting such distinction as mentioned above can be provided. Thus, diagnostic ability can be thereby improved.

INDUSTRIAL APPLICABILITY

In diagnosis of angiostenosis using the electrocardiography-gated scan of X-ray CT, a user is provided with a view image showing high display contrast and time resolution for a focused blood vessel. Additional information based on a view image can be thereby provided even for a case where distinction of angiostenosis and motion artifacts is difficult only with a CT image, and therefore diagnostic ability is improved.

DESCRIPTION OF NUMERICAL NOTATIONS

1 . . . X-ray tube, 2 . . . X-ray detector, 3 . . . rotating plate (turntable), 4 . . . top of bed, 5 . . . gantry, 6 . . . opening, 7 . . . control device, 8 . . . electrocardiograph, 9 . . . memory, 10 . . . console, 11 . . . computer, 12 . . . monitor, 14 . . . FOV, 15 . . . subject.

The invention claimed is:

1. An X-ray CT device comprising an X-ray generating part, an X-ray detecting part oppositely disposed to the X-ray generating part, a revolving mechanism part for revolving a pair of the X-ray generating part and the X-ray detecting part, an image processing part for creating a CT image of a subject on the basis of X-ray transmission images of the subject acquired at a plurality of positions along the circumferential direction of the revolution, and a display part for displaying the CT image, wherein:
the image processing part comprises:
a region-of-interest setting part which sets a region of interest in the CT image,
a data value converting part which converts a data value of the CT image in the region of interest to another value,
a forward projection part which performs forward projection of the CT image including the CT image of the ROI, in which the data value is converted, and the CT image of a region outside the ROI, from a virtual X-ray generating part to a virtual X-ray detecting part to calculate a pseudo X-ray transmission image, and
a difference calculating part which calculates difference between the X-ray transmission image and the pseudo X-ray transmission image to create a differential image.

2. The X-ray CT device according to claim 1, wherein:
the image processing part comprises an X-ray transmission image selecting part which selects, among the X-ray transmission images acquired at a plurality of the positions, an X-ray transmission image used by the difference calculating part configured to create the differential image.

3. The X-ray CT device according to claim 2, wherein:
the X-ray transmission image selecting part which selects, among the X-ray transmission images acquired at a plurality of the positions, an X-ray transmission image used for calculation of the CT image and/or an X-ray transmission image in which the region of interest is included in an imaging field of view.

4. The X-ray CT device according to claim 1, wherein:
the forward projection part which creates data of the false X-ray image by using, among a plurality of X-ray beams connecting each of a plurality of detecting elements of the virtual X-ray detecting part and the virtual X-ray generating part, only an X-ray beam passing through the region of interest.

5. The X-ray CT device according to claim 1, wherein:
the image processing part comprises a judging part which judges whether the CT image covers the whole subject or the CT image is a partial region CT image whose region is smaller than the whole subject in a plane perpendicular to the revolving axis of the revolution, and when the CT image is judged to be a partial region CT image by the judging part, configured to calculate a second CT image for a region other than the region of the partial region CT image, and the forward projection part configured to calculate the pseudo X-ray transmission image for the partial region CT image and the second CT image.

6. The X-ray CT device according to claim 1, wherein:
the region-of-interest setting part comprises a receiving part for receiving specification of position and shape of the region of interest in the CT image, and sets a region surrounded by a shape received by the receiving part and positioned on the basis of a position received by the receiving part as the region of interest.

7. The X-ray CT device according to claim 1, wherein:
the region-of-interest setting part comprises a threshold value receiving part for receiving specification of a threshold value of the CT value, and extracts the region of interest on the basis of comparison of the threshold value received by the threshold value receiving part and the data value of the CT image.

8. The X-ray CT device according to claim 7, wherein:
the threshold value receiving part receives first and second threshold values, and the region-of-interest setting part which extracts pixels having a CT value between the first threshold value and the second threshold value from pixels in the CT image as pixels in the region of interest.

9. The X-ray CT device according to claim 7, wherein:
the region-of-interest setting part comprises a part for expanding or reducing the region of interest.

10. The X-ray CT device according to claim 6, wherein:
the region-of-interest setting part comprises an exclusion region receiving part which receives specification of a region that is excluded from the region of interest in the CT image, and excludes the region received by the exclusion region receiving part from the region of interest.

11. The X-ray CT device according to claim 1, wherein:
the data value converting part which converts a data value of the CT image in the region of interest to a constant value.

12. The X-ray CT device according to claim 1, wherein:
the data value converting part comprises an interpolation part which calculates a data value of the region of interest from a data value of a region other than the region of interest by interpolation, and converts a data value of the CT image in the region of interest to the interpolated value.

13. The X-ray CT device according to claim 1, wherein:
the image processing part further comprises an adding part which adds a plurality of X-ray transmission images acquired at positions different for the angle direction of the revolution or a plurality of differential images created by the difference calculating part.

14. The X-ray CT device according to claim 13, wherein:
the adding part which adds a plurality of the X-ray transmission images acquired at positions different for the angle direction of the revolution to created an added image,
the forward projection part which calculates the pseudo X-ray transmission image for one X-ray image among a plurality of the X-ray transmission images, and
the difference calculating part which calculates a differential image of the added image and the pseudo transmission X-ray image.

15. The X-ray CT device according to claim 13, wherein:
the adding part further comprises an exposure time receiving part which receives specification of arbitrary imaging exposure time, and calculates number of images to be added in the addition on the basis of the imaging exposure time received by the exposure time receiving part performs the addition.

* * * * *